United States Patent [19]
Gorsuch

[11] Patent Number: 5,968,004
[45] Date of Patent: Oct. 19, 1999

[54] MICROPOROUS MEMBRANE SHEET PLASMA EXTRACTION CATHETER

[75] Inventor: Reynolds G. Gorsuch, Yountville, Calif.

[73] Assignee: Matria Healthcare, Inc., Marietta, Ga.

[21] Appl. No.: 08/935,399

[22] Filed: Sep. 23, 1997

[51] Int. Cl.$^6$ .............................. A61M 37/00; A61F 2/00
[52] U.S. Cl. ................................. 604/4; 424/424
[58] Field of Search ............................ 601/62; 424/424; 210/644, 195.2, 321.6; 604/4

[56] References Cited

U.S. PATENT DOCUMENTS

| | | |
|---|---|---|
| 4,769,037 | 9/1988 | Midcalf . |
| 4,950,224 | 8/1990 | Gorsuch et al. . |
| 5,002,054 | 3/1991 | Ash et al. . |
| 5,151,082 | 9/1992 | Gorsuch et al. . |
| 5,152,743 | 10/1992 | Gorsuch et al. . |
| 5,224,926 | 7/1993 | Gorsuch et al. . |
| 5,242,382 | 9/1993 | Gorsuch et al. . |
| 5,735,809 | 4/1998 | Gorsuch . |
| 5,755,790 | 5/1998 | Chevillon et al. . |

*Primary Examiner*—Corrine McDermott
*Assistant Examiner*—Cheryl L. Huseman
*Attorney, Agent, or Firm*—Knobbe, Martens, Olson & Bear, LLP

[57] ABSTRACT

An assembly for being implanted in a blood vessel for carrying out in vivo plasma separation incorporates a plasma extraction capsule formed of a microporous polymeric membrane sheet having a pore size capable of allowing diffusion of plasma, the capsule having one or more interior plasma flow channels and a catheter secured to the capsule and having at least one lumen in fluid communication with the one or more interior capsule channels.

33 Claims, 3 Drawing Sheets

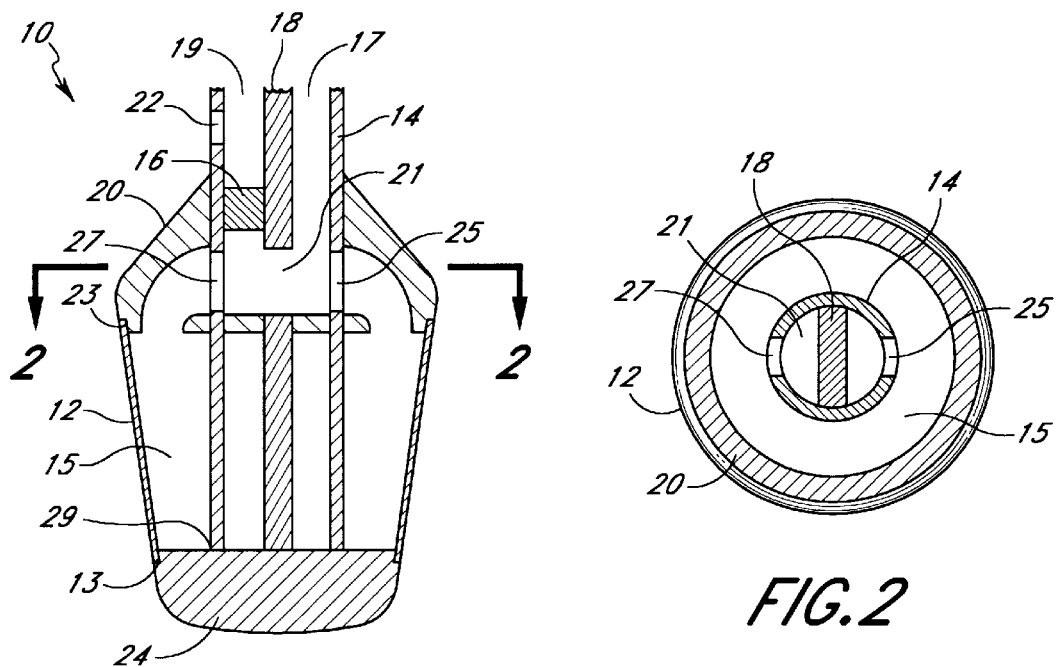
FIG. 1
FIG. 2
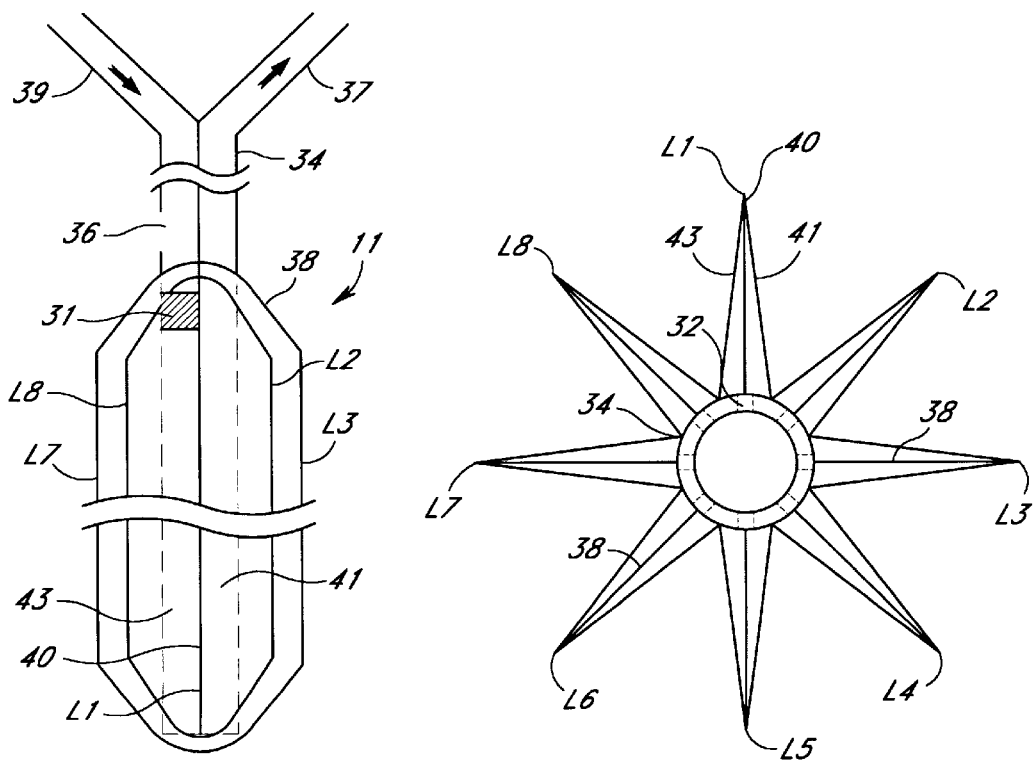
FIG. 3
FIG. 4

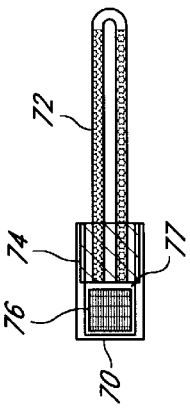
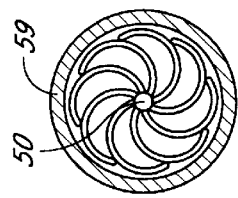
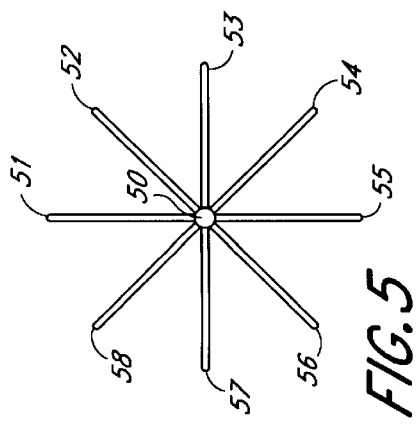
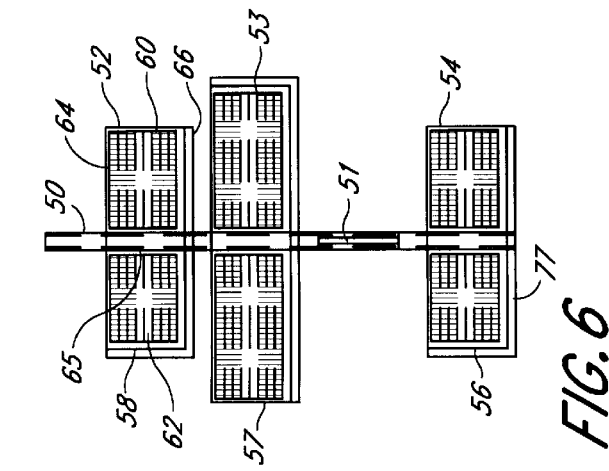
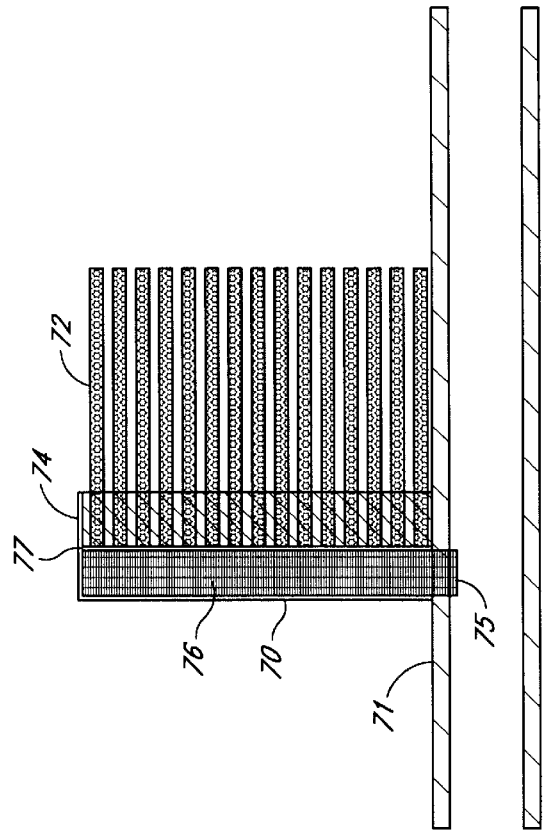

MICROPOROUS MEMBRANE SHEET PLASMA EXTRACTION CATHETER

BACKGROUND OF THE INVENTION

In U.S. Pat. Nos. 4,590,224, 5,151,082, 5,152,743, 5,224, 926 and U.S. Pat. No. 5,735,809 there are disclosed apparatus for in vivo separation of plasma from blood utilizing one or more hollow elongated microporous fibers implanted within a patient's blood vessel. The fibers are made of a microporous polymeric fiber membrane material having a pore size sufficient to allow diffusion of plasma into the hollow fiber interior but preventing cellular components larger than plasma to diffuse, ultrafiltrate or enter the fiber interior. The fiber or fibers are implanted within the blood vessel without significantly obstructing fluid flow through the vessel while providing the aforesaid in vivo plasma separation. The fiber assembly is secured in fluid communication with a catheter, preferably a dual lumen catheter having a first tube permitting plasma passage from the fiber and a second tube for returning plasma to the blood vessel after treatment. Various configurations and methods of fabrication as well as materials having a variety of characteristics and performance abilities are disclosed in the aforesaid patents and application as are various systems, apparatus, components and methods for use including measurement of blood parameters, kidney dialysis, and separation and removal of a substantial number of specific materials and plasma components, the descriptions of which are incorporated herein by reference. As efficient as the aforesaid hollow fiber loops are in separating blood plasma, it has been found that the hollow fibers may not provide the most optimum means of in vivo plasma extraction in all applications, treatment protocols, or in all patients.

SUMMARY OF THE INVENTION

The present invention provides an improved plasma extraction element using a membrane sheet which may be formed into and used in a variety of different configurations, morphologies and shapes capable of performing the same plasma extraction function as the aforesaid hollow fiber assembly devices. The use of such membrane sheets provides for a variety of different plasma extraction devices having improved physical and more efficient performance capabilities.

BRIEF DESCRIPTION OF THE DRAWINGS

FIG. 1 is a schematic side sectional elevation of a tubular plasma extraction capsule incorporating a microporous polymeric membrane sheet according to the invention;

FIG. 2 is a view taken along line A—A of FIG. 1;

FIG. 3 is a schematic side view of a corrugated plasma extraction capsule configuration having a plurality of elongated lobes formed of membrane sheets;

FIG. 4 illustrates an enlarged end view of the capsule of FIG. 3;

FIG. 5 is an end view of another embodiment showing a plasma extraction device formed of folded membrane sheets;

FIG. 6 is a side view of the assembly of FIG. 5;

FIG. 7 schematically illustrates a device of FIG. 5 positioned within a blood vessel;

FIGS. 8 and 9 illustrate a plasma extraction capsule formed according to the invention using both sheet membranes and hollow fiber membranes, FIG. 8 representing an end view of one lobe of such a device and FIG. 9 a side view thereof, the lobe being attached to a catheter;

DETAILED DESCRIPTION OF THE PREFERRED EMBODIMENT

Figure 11:
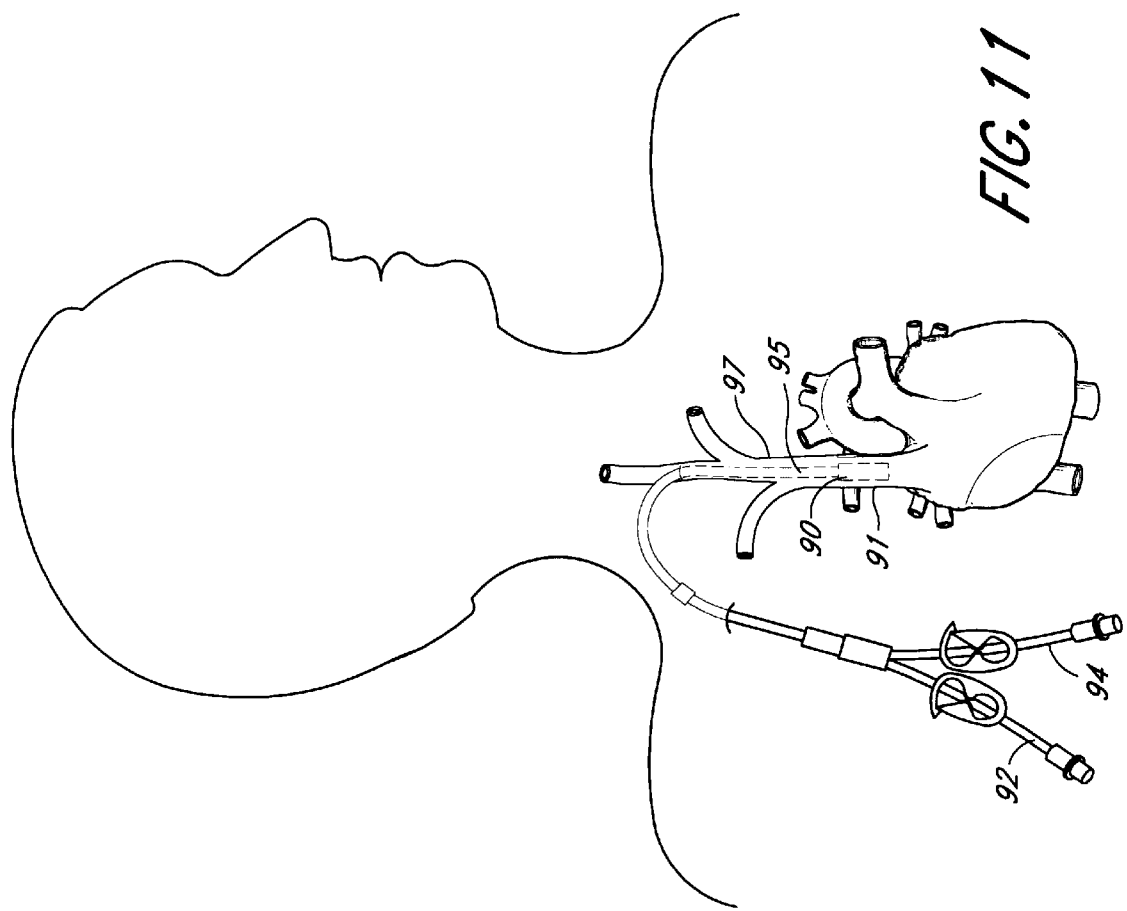
FIG. 11 illustrates implant positioning of a device according to the invention.

In FIGS. 1 and 2 there is shown a plasma extraction capsule assembly 10 formed of a microporous polymeric membrane sheet 12 in the form of a tapered or conical tube formed by securing one edge 23 of the tubular sheet on a first header 20 and a second opposite edge 13 of the tubular sheet on a terminal header 24. The capsule is secured at an end of dual lumen catheter 14 a portion of which also extends through the capsule interior. It may be preferred to pot or glue the end 29 of the dual lumen catheter in the terminal header 24 as illustrated. Within the capsule, the side walls of the catheter are provided with ports 25 and 27 communicating with the capsule interior 15 and the plenum 21 of the catheter. The catheter plenum communicates with the outflow lumen 17. Wall 18 divides the catheter and separates outflow lumen 17 and plasma return lumen 19. A plug or block 16 is positioned along the end of the return lumen downstream from plasma return port 22 to occlude the return lumen 19 between the plasma return port 22 and the plenum 21 of the capsule. It will be observed that the interior chamber 15 of the plasma extraction capsule is in fluid communication with the outflow plenum 17 of the dual lumen catheter 14 via plenum 21 whereby plasma diffusing through the membrane 12 passes through the capsule and into the plasma outflow lumen 17.

The specific location of the ports 25 and 27 along the catheter interiorly of the capsule are not limited to the positions illustrated in FIG. 1. For example, they may be located closer to terminal header 24, whereby more of the plasma exudate is routed along the catheter interior to the outflow catheter lumen. Moreover, the number of such ports may be increased or decreased, for example, a plurality of such ports may be positioned along the length of the catheter portion extending within the capsule, so long as there is no mixing of the plasma directed into the outflow lumen 17 with the return flow of treated plasma along return lumen 19. The size of the capsule must be such that it is capable of being implanted in a patient's blood vessel. The length of the capsule and the surface area of the membrane sheet to be exposed to the flow of blood within the vessel may also be selected to accomplish the rate of plasma separation in the vessel in which the device is to be implanted, which can be readily determined and selected by those skilled in the art.

The shape of the tubular capsule may be cylindrical or it may be tapered or conical as illustrated, the latter being preferred for increased shear rate of blood at the membrane surface. By increasing the angle of the membrane sheet relative to the axis of blood flow in the vein offers improved trans-membrane flux performance. Moreover, the angle of the tapered or slanted sheet need not necessarily be flat or planar along the entire membrane surface. Thus, other side profile shapes and configurations of the tubular membrane sheet may be used to achieve desired and improved performance.

FIGS. 3 and 4 illustrate a corrugated capsule embodiment of the invention. The elongated corrugations define a plurality of elongated hollow lobes (L1–L8) using flat sheets or portions of sheets of the microporous polymeric membrane which are folded or bonded to form alternating ridges and grooves. A dual lumen catheter 34 having an outlet flow channel 37 and a return or inlet channel or lumen 39 extends along the interior of the elongated corrugated capsule 11. In FIG. 3 the portion of the catheter secured along the capsule is illustrated by the dashed lines. The return lumen 39 includes an outlet port 36 through which treated plasma is returned to the patient's vessel. A plug 31 occluding the return lumen of the catheter is positioned downstream from port 36. The remaining interior lumen of the catheter extending along the capsule provides a plasma outflow plenum in fluid communication with the outlet lumen 37.

The ridges of lobes L1–L8 may be formed by bonding the edges of adjacent sheets. Observing FIG. 4, sheets 41 and 43 are shown joined along their edges to form ridge 40 of lobe L1. Alternatively, a membrane sheet may be folded or creased to form one or more of the ridges. The other edge of each of the membrane sheets or sheet portions are secured at or adjacent to the exterior surface of catheter 34 to form the grooves of the corrugated capsule structure. Each of the adjacent edges of the membrane sheet portions can be individually secured or bonded to the exterior of the catheter to form the grooves, or the adjacent edges of the sheets or sheet portions can be bonded together and the secured edges bonded to the catheter surface. Alternatively, one or more or all of the grooves may be formed by creasing the membrane sheet or sheet portions, which crease then may be secured along the exterior catheter surface. It will also be noted that the leading and trailing edges of the adjacent membrane sheet portions are joined by bonding, one of such edges 38 on lobe L3 being illustrated in both FIGS. 3 and 4. Again, such bonding will be necessary both for the leading and trailing edges, i.e., at both ends of the elongated capsule. The interior plenum of the catheter extending along the capsule is in fluid communication with the hollow interior of each of the capsule lobes via a port 32 shown by dashed lines.

The corrugated capsule structure of FIGS. 3 and 4 provides a substantially enlarged membrane surface area exposed within the patient's blood vessel to the blood for increasing the rate of diffusion through the membrane into the capsule. The efficiency of the elongated corrugated capsule of this embodiment may be further improved by twisting the capsule along its axis to present an angled membrane surface to the flow of blood within the vessel thereby optimizing shear rate of blood flow at the membrane surface. The degree of twist may be determined and selected, depending on the number of lobes used, length of the capsule, cross-sectional dimension or depth of the lobes, blood flow, etc. as will be understood by those skilled in the art. Although eight lobes are illustrated in the embodiment, any desired number of lobes may be used, as well as variation and selection of the capsule length, diameter, etc. to meet the patient's prescription and protocol.

FIGS. 5 and 6 illustrate yet another preferred embodiment of a plasma extraction capsule formed of a polymeric membrane sheet using segments which may be folded, creased or bonded along their edges to form a series of substantially flat or flattened envelopes of opposing sheets or portions of sheets which are secured to and extend radially from the catheter. In FIG. 5, an end view of such an assembly is illustrated and in FIG. 6 a side view showing panels 51–58 extending radially from catheter 50. Each panel 60 is composed of an upper and lower or top and bottom membrane strip which is creased along edge 64 and bonded by heat sealing or adhesive along the opposite side edge 66. Interiorly of these panels or envelopes is a flow directing member in the form of a filler mesh strip 62, preferably polymeric or metallic, providing a passageway for the plasma which has diffused through the membrane pores. The strip is bonded or otherwise secured in fluid communication with the catheter 50. The mesh strip thus provides an elongated channel or chamber within the envelope or panel through which the plasma flows to the catheter. Each mesh strip is in fluid communication with the catheter lumen via a port 65. The mesh strip is only one example of a flow directing member, and other equivalent means include perforated tubes, open cell foam devices, screens, etc. Thus, any device capable of providing the desired plasma flow along the interior of the envelope, is chemically and biologically compatible with the membrane, and can be installed in the envelope may be used for the aforesaid purpose.

The edges of the membrane panels are bonded to the catheter to form the plasma extraction assembly. Although eight panels or envelopes are shown in the example of FIGS. 5 and 6, any number of panels may be used, and the length and dimensions of the panels may also be selected to provide the desired surface area, again depending on the flow rate of plasma desired. The assembly illustrated uses opposing pairs of panels radiating from the catheter. However, other configurations may be used whereby the panels may be positioned in an alternate fashion around the circumference of the catheter. The shape of the panels may also be varied, and instead of being rectangular, may be arch-shaped, elliptical, or even irregularly shaped where such configurations would offer desirable or improved plasma diffusion or flow effects. Moreover, the different panels may also be twisted along their lengths between the catheter and the outer edge of each panel whereby the surface angle of each panel presented to the blood flow along the vessel is improved to optimize the shear rate of blood flow at the membrane surface. The degree of twist may be determined and selected as desired to optimize the desired shear and exposure surface area along the blood flow axis.

FIG. 7 illustrates an example of a sheet membrane design assembly of FIG. 5 within a blood vessel 59, with the length of the different panels or envelopes being somewhat greater than the radius of the blood vessel in which the assembly is implanted. Of course, the length of each or different ones of the panels or envelopes need not be as long as the radius of the vessel in which the assembly is to be implanted, and may be equal to or shorter than such radius dimension.

FIGS. 8 and 9 illustrate another preferred embodiment of a plasma extraction assembly using a combination of sheet membranes such as shown in FIGS. 5 and 6 and hollow fiber membranes. A plurality of hollow fiber membranes 72 are secured in a header 74 along the sheet membrane 76 to form the lobe 70 which is secured to and extends from catheter 71. The hollow fibers are fully described in U.S. Pat. Nos. 5,224,926 and 5,735,809, both of which disclosures are incorporated herein by reference. Observing also FIGS. 5 and 6, the hollow fiber membrane 72 is potted or otherwise bonded to the outer surface of a membrane sheet lobe, whereby the elongated axis of each of the hollow fibers preferably extends axially along the axis of the catheter 71. The fibers are shown extending from the leading edge 77 of the edge facing the blood flow in the vessel. As illustrated, each of the hollow fibers 72 is aligned so that both legs of the hollow fiber are coaxial and coplanar with the elongated axis of the catheter 71, shown particularly in FIG. 9. However, the fibers need not be so aligned, and may be slanted, or even twisted somewhat along their respective axes such as described in the aforesaid application 764,631.

The number of fibers used with each panel may also be varied, depending on the overall or total flat membrane and fiber surface to be exposed to the blood in the vessel. As previously described in the embodiments shown in FIGS. 5 and 6, the interior of each of the envelope lobes preferably contain a filler mesh strip or other flow directing component providing a fluid communication channel or cavity between the hollow fibers with the interior lumen of catheter 71. As shown in FIG. 9, the end 75 of sheet membrane 76 is secured in fluid communication with the lumen of catheter 71. Such a configuration allows for blood plasma to diffuse through each of the hollow fiber membranes 72, into the interior passageway of the envelope or panel 76, and along the panel to the lumen of catheter 71 where the plasma is then directed ex vivo for plasma treatment.

Figure 10:
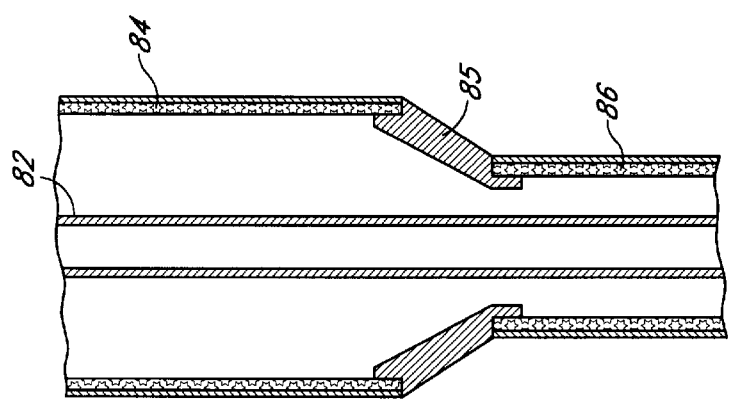
FIG. 10 illustrates a partial sectional view of a tubular sheet membrane extraction assembly having tubes of different diameters for use in different sized blood vessels.

The assembly illustrated in FIG. 10 represents two plasma extraction capsules of the type shown in FIGS. 1 and 2 which have been assembled end to end or in series, each of the two capsules being of different size (radius). Capsule 84 has a larger radius as compared to capsule 86, and which capsules are joined by a header 85. Both of the capsules extend along a common axis with catheter 82, each of the capsules being of the sheet or tubular type membrane design illustrated in FIGS. 1 and 2, although they are shown as having a substantially cylindrical shape rather than the tapered shape of the embodiment of FIG. 1. However, the exterior shape is not critical, and may be designed as previously described regarding FIG. 1. The series or end-to-end configuration of FIG. 10 is to accommodate different sizes of vein structures, for example, allowing such a device to be implanted both in the subclavian vein and the vena cava. Thus, the assembly may be implanted whereby capsule 84 is positioned in the larger vessel, and capsule 86 in the smaller vessel. The distance between the two capsules, for example, the length and shape of header 85 is shown by way of example only, and one or more headers may be used having any suitable shape for accommodating the intended use in the different and contiguous vessels.

Typical implantation of the catheter and plasma extraction capsule is in the superior vena cava via either the subclavian or interior jugular vein using a percutaneous procedure practiced by those skilled in the art. A preferred site is just above the right ventricle as illustrated in FIG. 11. FIG. 11 illustrates the implantation of a plasma extraction capsule 90 in a vessel 91 (vena cava) with catheter 95 extending along the jugular vein 97. The two catheter extenders 92 and 94 allow the plasma to flow in and out of the capsule, respectively; and to and from the plasma treatment assembly apparatus as described in the aforesaid incorporated patents.

The sheet membranes used in the different embodiments may be made from flat sheet membrane materials known as Micro-PES membranes manufactured by Akzo Nobel, constructed of polyethersulfone, a hydrophilic polymeric material which is required for the uses described herein. Such a membrane is available in a broad range of trans-membrane flux (flow) characteristics between specification ranges of 4 and 260 ml/min/cm$^2$ (water @ 25° C.)/bar. Sieving coefficients are controllable by pore size process control with useful pore sizes of between 0.001 $\mu$ and 1$\mu$. The selection of the specific sheet membrane material as well as its use and process for forming the capsule having the desired configuration and characteristics within the scope of the invention as described herein will be evident to those skilled in the art.

What is claimed is:

1. An assembly for being implanted in a blood vessel for carrying out in vivo plasma separation comprising:

a plasma extraction capsule comprising a plurality of panels or lobes formed of a microporous polymeric membrane sheet having a pore size capable of allowing plasma to diffuse therethrough, said capsule having one or more plasma flow channels therein, and a catheter secured to said capsule and comprising at least one lumen in fluid communication with said one or more plasma flow channels.

2. An assembly of claim 1, wherein said catheter extends along at least a portion of the interior of said capsule.

3. An assembly of claim 2, wherein said catheter is a dual lumen catheter having a first passageway in fluid communication with the interior of said capsule for directing plasma therefrom and a second passageway having a port for communicating with a blood vessel for returning plasma thereto.

4. An assembly of claim 1, including a header secured to said catheter and said membrane sheet.

5. An assembly of claim 1 wherein said capsule comprises a corrugated tube having a plurality of lobes formed by said membrane set.

6. An assembly of claim 5, wherein said corrugated tube comprises grooves and ridges formed along said membrane sheet.

7. An assembly of claim 5, wherein said corrugated tube comprises a plurality of elongated membrane sheets each sheet joined to an adjacent sheet.

8. An assembly of claim 7, wherein a portion of said catheter extends along the interior of said capsule and wherein each of said elongated membrane sheets is secured to said catheter.

9. An assembly of claim 8, wherein said corrugated tube comprises a plurality of lobes and wherein said catheter portion extending along the interior of said capsule includes a plurality of ports each in fluid communication with one of said lobes.

10. An assembly of claim 9, wherein said catheter is a dual lumen catheter having a first passageway in fluid communication with the interior of said capsule for directing plasma therefrom and a second passageway having a port for communicating with a blood vessel for returning plasma thereto.

11. An assembly of claim 9, wherein each of said elongated membrane sheets have a first edge joined to the first edge of an adjacent elongated membrane sheet to form an elongated ridge, and a second edge secured along said catheter to form an elongated groove, and wherein said lobes are elongated lobes formed by said elongated ridges and grooves.

12. An assembly of claim 1, comprising a plurality of panels each panel comprising an envelope formed of opposite segments of said microporous polymeric membrane sheet said assembly having a fluid directing member secured between said opposite segments forming said plasma flow channel.

13. An assembly of claim 12, wherein said envelope comprises a folded polymeric membrane sheet and wherein the edges of said sheet are joined to enclose said capsule.

14. An assembly of claim 12, wherein said panels extend radially from said catheter.

15. An assembly of claim 14, wherein the opposite segments lie along substantially parallel planes extending radially from said catheter.

16. An assembly of claim 14, wherein said capsule comprises pairs of panels each panel of a pair extending from said catheter opposite the other panel of said pair.

17. An assembly of claim 15, wherein said capsule comprises pairs of panels each panel of a pair extending from said catheter opposite the other panel of said pair.

18. An assembly of claim 12, wherein each of said panels is elongated along a different axis extending radially from said catheter.

19. An assembly of claim 12, including a plurality of elongated microporous hollow polymeric fiber loops secured in fluid communication with one or more of said plurality of panels.

20. An assembly of claim 19, wherein each of said fiber loops has a pair of ends secured adjacent to a panel and wherein the hollow interior of each said fiber is in fluid communication with the plasma flow channel of said panel.

21. An assembly of claim 14, including a plurality of elongated microporous hollow polymeric fiber loops secured in fluid communication with one or more of said plurality of panels.

22. An assembly of claim 21, wherein each of said fiber loops has a pair of ends secured adjacent to a panel and wherein the hollow interior of each said fiber is in fluid communication with the plasma flow channel of said capsule.

23. An assembly of claim 19, wherein said plurality of fiber loops are spaced substantially uniformly along said panels.

24. An assembly of claim 21, wherein said plurality of fiber loops are spaced substantially uniformly along said panels.

25. An assembly of claim 23, wherein each of said panels is elongated along a different axis extending radially from said catheter.

26. An assembly of claim 25, wherein the fiber loops extending from each panel extend substantially normal to the radial axis of each said panel, respectively.

27. An assembly of claim 26, wherein said plurality of fiber loops are secured along the elongated axis of each respective panel.

28. An assembly of claim 1, comprising a plurality of said capsules, each capsule having a different cross-sectional diameter.

29. An assembly of claim 28, compromising a first cylindrical capsule having a first diameter for being transplanted in a first blood vessel and second cylindrical capsule having a second diameter for being transplanted in a second blood vessel.

30. An assembly of claim 29, wherein said first and second capsules extend along a common axis.

31. An assembly of claim 1, wherein said pore size of said membrane sheet is between $0.001\mu$ and $1\mu$.

32. An assembly of claim 1, wherein said membrane sheet has a transmembrane flux of between 4 and 260 ml/min/cm$^2$ (water @ 25° C.)/bar.

33. A method of forming a plasma extraction device for in vivo separation of plasma from blood comprising:
forming a plurality of plasma extraction lobes or panels using a plurality of membrane sheets having a pore size between $0.001\mu$ and $1\mu$, folding each of said sheets and joining the adjacent edges of each said folded sheet to form generally flat lobes or panels, and securing each of said lobes or panels along a catheter.

* * * * *